(12) United States Patent
Chandrasekaran et al.

(10) Patent No.: US 7,297,157 B2
(45) Date of Patent: Nov. 20, 2007

(54) MEDICAL DEVICE WITH RADIOPACITY

(75) Inventors: Verivada Chandrasekaran, Mercer Island, WA (US); Karl Morris Schmidt, Seattle, WA (US); Christopher Torres Molina, Redmond, WA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 10/629,934

(22) Filed: Jul. 29, 2003

(65) Prior Publication Data

US 2004/0068315 A1    Apr. 8, 2004

Related U.S. Application Data

(63) Continuation of application No. 10/263,212, filed on Oct. 2, 2002, now Pat. No. 6,638,301.

(51) Int. Cl.
*A61F 2/06*    (2006.01)

(52) U.S. Cl. .................... 623/1.34; 623/1.44

(58) Field of Classification Search .......... 623/427, 623/2.1–2.31, 1.11–1.44, 1.15–1.34; 427/2.1–2.31; 600/3
See application file for complete search history.

(56) References Cited

U.S. PATENT DOCUMENTS

| | | | |
|---|---|---|---|
| 5,222,971 A * | 6/1993 | Willard et al. ............. 606/198 |
| 5,234,457 A | 8/1993 | Andersen |
| 5,593,438 A | 1/1997 | Akhavi et al. |
| 5,630,840 A | 5/1997 | Mayer |
| 5,674,242 A | 10/1997 | Phan et al. |
| 5,725,570 A | 3/1998 | Heath |
| 5,824,049 A | 10/1998 | Ragheb et al. |
| 5,858,556 A | 1/1999 | Eckert et al. |
| 6,099,561 A * | 8/2000 | Alt ............................ 623/1.44 |
| 6,174,329 B1 * | 1/2001 | Callol et al. .............. 623/1.34 |
| 6,248,190 B1 | 6/2001 | Stinson |
| 6,261,320 B1 * | 7/2001 | Tam et al. ................. 623/1.15 |
| 6,287,249 B1 * | 9/2001 | Tam et al. ..................... 600/3 |
| 6,315,794 B1 | 11/2001 | Richter |
| 6,334,871 B1 | 1/2002 | Dor et al. |
| 6,471,721 B1 | 10/2002 | Dang |
| 6,676,700 B1 * | 1/2004 | Jacobs et al. ............. 623/1.34 |
| 6,908,480 B2 * | 6/2005 | Jayaraman ................ 623/1.42 |
| 2002/0058989 A1 | 5/2002 | Chen et al. |
| 2003/0028241 A1 * | 2/2003 | Stinson ..................... 623/1.15 |
| 2003/0074054 A1 * | 4/2003 | Duerig et al. ............ 623/1.15 |
| 2003/0144728 A1 * | 7/2003 | Scheuermann et al. .... 623/1.15 |
| 2003/0191520 A1 * | 10/2003 | Pelton ....................... 623/1.15 |
| 2004/0015229 A1 * | 1/2004 | Fulkerson et al. ........ 623/1.22 |
| 2004/0039438 A1 * | 2/2004 | Alt ............................ 623/1.15 |
| 2004/0054399 A1 * | 3/2004 | Roth .......................... 623/1.16 |

FOREIGN PATENT DOCUMENTS

| | | |
|---|---|---|
| EP | 0 824 900 A2 | 2/1998 |
| WO | WO 99/02195 | 1/1999 |
| WO | WO 02/05863 | 1/2002 |
| WO | 02/39927 | 5/2002 |

OTHER PUBLICATIONS

PCT Partial Search Report (Form PCT/ISA/206) dated Feb. 12, 2004.
Communication from European Patent Office.

* cited by examiner

*Primary Examiner*—Suzette Gherbi
(74) *Attorney, Agent, or Firm*—Fish & Richardson P.C.

(57) ABSTRACT

An endoprosthesis, such as a stent, having a layer that can enhance the biocompatibility of the endoprosthesis, and methods of making the endoprosthesis are disclosed.

20 Claims, 4 Drawing Sheets

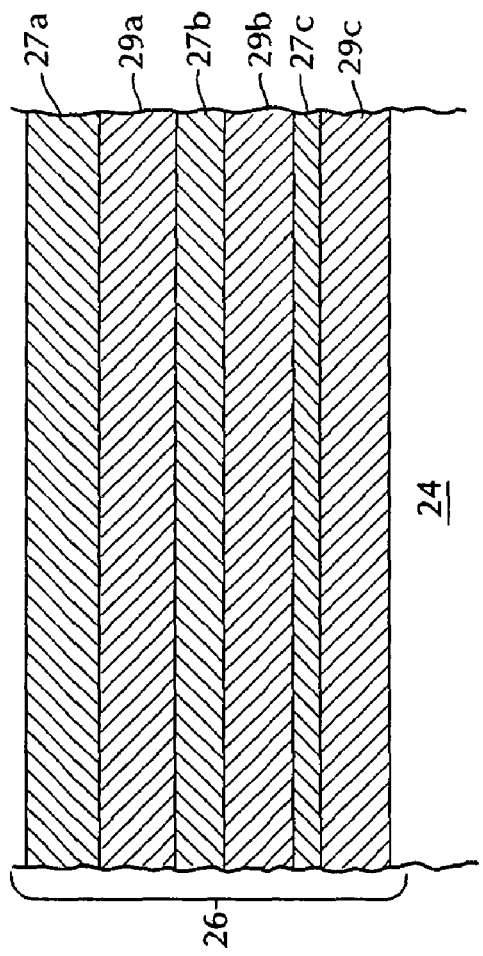
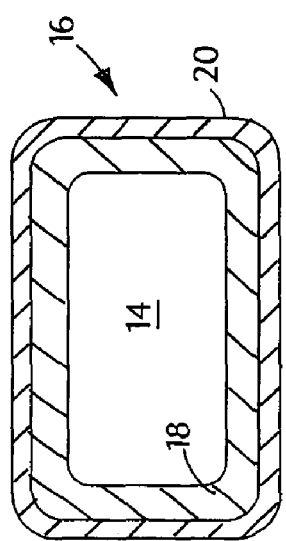
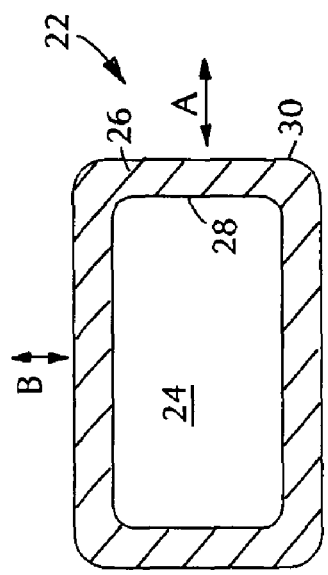

FIG. 7

| Sputter Cleaning Parameters (Ion Beam) | | Deposition Sputtering Parameters (Ion Beam) | | Deposition Parameters (Electron Beam Evaporation) | |
|---|---|---|---|---|---|
| Gas type | Argon | Gas type | Argon | Pressure | ≤1×10$^{-4}$ Torr |
| Flow | 2.5-3.5 sccm | Flow | 2.5-3.5 sccm | Deposition rate | 3.5-3.5 Å/sec |
| Energy | 1-2 keV | Energy | 1-3 keV | Energy | 8 keV |
| Power | 58-65 Watts | Power | 58-65 Watts | Power | 2.9 kW |
| Current | 10-35 mA | Current | 15-35 mA | Current | 0.375 A |
| Time | 20-30 min | | | | |

FIG. 8

| Sputter Cleaning Parameters (Ion Beam) | | Deposition Sputtering Parameters (Ion Beam) | | Deposition Parameters (Electron Beam Evaporation) | |
|---|---|---|---|---|---|
| Gas type | Argon | Gas type | Argon | Pressure | 3.5×10$^{-5}$ Torr |
| Flow | 2 sccm | Flow | 2 sccm | Deposition rate | 4-5 Å/sec |
| Energy | 2 keV | Energy | 2 keV | Energy | 8 keV |
| Power | 60 Watts | Power | 80 Watts | Power | 1.76 kW |
| Current | 15 mA | Current | 18 mA | Current | 0.226 A |
| Time | 20 min | | | | |

FIG. 9

| Sputter Cleaning Parameters (Ion Beam) | | Deposition Sputtering Parameters (Ion Beam) | | Deposition Parameters (Electron Beam Evaporation) | |
|---|---|---|---|---|---|
| Gas type | Argon | Gas type | Argon | Pressure | 1.2×10$^{-4}$ Torr |
| Flow | 3 sccm | Flow | 2 sccm | Deposition rate | 2-3 Å/sec |
| Energy | 1 keV | Energy | 1 keV | Energy | 7.5 keV |
| Power | 60 Watts | Power | 60 Watts | Power | 2.0 kW |
| Current | 25 mA | Current | 32 mA | Current | 0.15 A |
| Time | 30 min | | | | |

MEDICAL DEVICE WITH RADIOPACITY

CROSS-REFERENCE TO RELATED APPLICATIONS

This application is a continuation application of and claims priority to U.S. application Ser. No. 10/263,212, filed on Oct. 2, 2002 now U.S. Pat No. 6,638,301, the entire contents of which are hereby incorporated by reference.

TECHNICAL FIELD

The invention relates to medical devices, such as, for example, stents and stent-grafts, and methods of making the devices.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced, or even replaced, with a medical endoprosthesis. An endoprosthesis is typically a tubular member that is placed in a lumen in the body. Examples of endoprosthesis include stents and covered stents, sometimes called "stent-grafts".

Endoprostheses can be delivered inside the body by a catheter that supports the endoprosthesis in a compacted or reduced-size form as the endoprosthesis is transported to a desired site. Upon reaching the site, the endoprosthesis is expanded, for example, so that it can contact the walls of the lumen.

The expansion mechanism may include forcing the endoprosthesis to expand radially. For example, the expansion mechanism can include the catheter carrying a balloon, which carries a balloon-expandable endoprosthesis. The balloon can be inflated to deform and to fix the expanded endoprosthesis at a predetermined position in contact with the lumen wall. The balloon can then be deflated, and the catheter withdrawn.

In another delivery technique, the endoprosthesis is formed of an elastic material that can be reversibly compacted and expanded, e.g., elastically or through a material phase transition. During introduction into the body, the endoprosthesis is restrained in a compacted condition. Upon reaching the desired implantation site, the restraint is removed, for example, by retracting a restraining device such as an outer sheath, enabling the endoprosthesis to self-expand by its own internal elastic restoring force.

To support a passageway open, endoprostheses are sometimes made of relatively strong materials, such as stainless steel or Nitinol (a nickel-titanium alloy), formed into struts or wires. These materials, however, can be relatively radiolucent. That is, the materials may not be easily visible under X-ray fluoroscopy, which is a technique used to locate and to monitor the endoprostheses during and after delivery. To enhance their visibility (e.g., by increasing their radiopacity), the endoprostheses can be coated with a relatively radiopaque material, such as gold. Because the endoprostheses are typically kept in the body for a relatively long time, it is desirable that they have good biocompatibility.

SUMMARY

The invention relates to methods of making medical devices, such as, for example, stents and stent-grafts, and methods of making the devices. More particularly, the invention features an endoprosthesis, such as a stent, having a layer that can enhance the biocompatibility of the endoprosthesis.

In one aspect, the invention features a stent including a member having a first portion, and a second portion disposed outwardly of the first portion. The second portion is more radiopaque than the first portion and has a first layer including a radiopaque material, and a second layer defining an outer surface of the member and including the radiopaque material and a second material.

Embodiments may include one or more of the following features. The second layer includes an alloy of the radiopaque material and the second material. The radiopaque material is selected from the group consisting of gold, platinum, palladium, and tantalum. The second material is selected from the group consisting of titanium, chromium, palladium, niobium, and silicon. The first portion includes a material selected from the group consisting of stainless steel and nickel-titanium alloy.

The first portion can be the innermost portion of the member, and/or contact the second portion.

The stent can further include a third portion between the first portion and the second portion, a polymeric layer on the member, and/or a drug-releasing layer on the member.

In another aspect, the invention features a stent including a member having a first portion having a first layer including a radiopaque material, and a second layer defining an outer surface of the member and including the radiopaque material and a second material.

In another aspect, the invention features a stent including a member having a first portion, and a second portion disposed outwardly of the first portion. The second portion is more radiopaque than the first layer and includes a first layer having a radiopaque material, and a second layer including the radiopaque material and defining an outer surface of the member, the second layer having a lower oxidation potential than an oxidation potential of the first layer.

Embodiments may include one or more of the following features. The radiopaque material is selected from the group consisting of gold, platinum, palladium, and tantalum. The second layer includes an alloy of the radiopaque material and a second material. The second material is selected from the group consisting of titanium, niobium, palladium, chromium, and silicon.

The first portion can include a material selected from the group consisting of stainless steel and a nickel-titanium alloy. The first portion can be the innermost portion of the member. The first portion can contact the second portion.

The first and second portions can have different compositions.

The stent can further include a polymeric layer on the member and/or a drug-releasing layer on the member.

In another aspect, the invention features a stent having a member having a first portion including a first layer comprising a radiopaque material, and a second layer comprising the radiopaque material and defining an outer surface of the member. The second layer has a lower oxidation potential than an oxidation potential of the first layer.

In another aspect, the invention features a stent having a member including a first portion having a concentration gradient of a radiopaque material, the first portion defining an outer surface of the member.

Embodiments may include one or more of the following features. The concentration of the radiopaque material increases as a function of distance from the outer surface. The concentration gradient varies substantially linearly along a thickness of the first portion. The radiopaque material is selected from a group consisting of gold, platinum, palladium, and tantalum. The first portion is formed of an alloy including the radiopaque material and a second material. The member further includes a second portion disposed inwardly of the first portion, the second portion being more radiolucent than the first portion.

In another aspect, the invention features a method of making a stent including a member. The method includes forming an outer layer on the member having a radiopaque material and a second material, and oxidizing a portion of the outer layer.

Embodiments may include one or more of the following features. Oxidizing the portion includes forming an oxide or a nitride from the outer layer. The method further includes forming a radiopaque layer having the radiopaque material. The outer layer is formed with a compositional gradient.

The outer layer is formed by a process selected from the group consisting of physical vapor deposition, chemical vapor deposition, and electrodeposition.

Oxidizing the portion of the outer layer can be performed by electropolishing, by heating the outer layer in an oxidizing environment, and/or by ion implanting oxygen in the outer layer and heating the outer layer.

The method can further include forming a polymeric layer on the outer layer, and/or forming a drug-releasing layer on the outer layer.

Other aspects, features and advantages of the invention will be apparent from the description of the preferred embodiments thereof and from the claims.

DESCRIPTION OF DRAWINGS

FIG. 2 is a schematic, cross-sectional view of the stent of FIG. 1, taken along line 2—2.

FIG. 3 is a schematic, cross-sectional view of a strut of an embodiment of a stent.

FIG. 4 is a schematic, partial cross-sectional view of a strut of an embodiment of a stent.

FIG. 7 is a table of parameters for an ion beam assisted deposition process.

FIG. 8 is a table of parameters for an ion beam assisted deposition process.

FIG. 9 is a table of parameters for an ion beam assisted deposition process.

DETAILED DESCRIPTION

Figure 1:
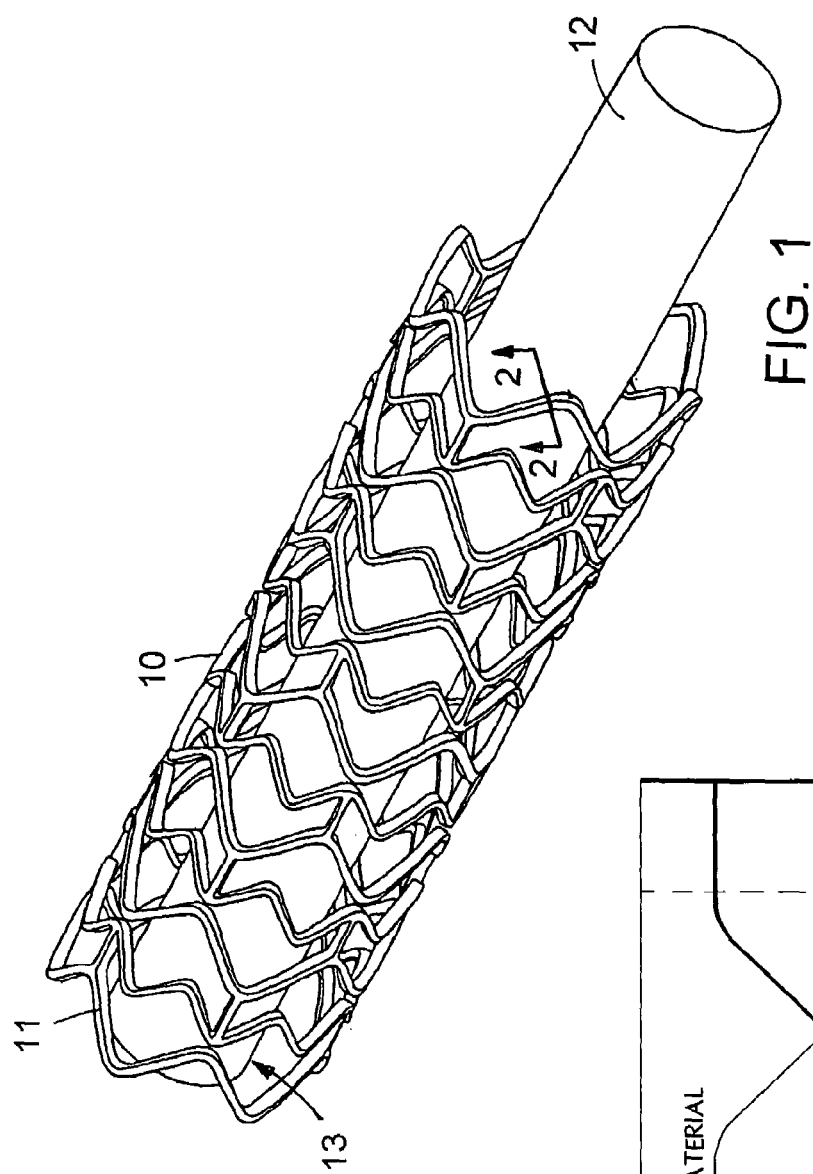
FIG. 1 is a perspective view of an embodiment of a stent.

FIG. 1 shows a support 12 carrying a stent 10, which is in the form of a tubular member defined by struts 11 and openings 13. Depending on the type of stent 12 (e.g., balloon-expandable or self-expandable), support 12 can be a balloon catheter or a catheter shaft. Referring to FIG. 2, stent 10 includes multiple cross-sectional portions. In particular, struts 11 of stent 10 are formed of a relatively radiolucent core 14 surrounded by a relatively radiopaque portion 16. Radiopaque portion 16 includes a radiopaque layer 18, e.g., made of gold, and a layer 20, e.g., made of a gold-titanium alloy, that can enhance the biocompatibility of stent 10. For example, layer 20 can be passivated to provide stent 10 with a relatively inert outer surface.

In general, stent 10 can be formed by coating a relatively radiolucent stent with a radiopaque material, such as gold or platinum, to form layer 18. Layer 20 is then formed on the radiopaque material. Layer 20 can be formed on the pre-formed radiopaque layer 18 and/or formed from a portion of the radiopaque layer. Layer 20 is then passivated, e.g., by forming a layer of an oxide or nitride on layer 20 or by converting layer 20 to an oxide or a nitride.

Core 14 is generally formed of one or more core material selected to provide stent 10 with certain physical and mechanical properties. For example, the core material is selected to provide stent 10 with sufficient hoop strength and radial strength so the stent can maintain a body vessel open. Suitable core materials include stainless steel (e.g., 316L stainless steel), Nitinol (e.g., for self-expandable stents), other titanium alloys, tantalum alloys, zirconium alloys, and/or niobium alloys. At the same time, it is also desirable to reduce (e.g., minimize) differences or mismatch in mechanical properties (e.g., stiffness) between the stent and the body vessel. The mechanical mismatch can cause, for example, inflammation and/or reocclusion of the vessel. One method of reducing mechanical mismatch is to form the stent with less material (e.g., by forming smaller struts 11), thereby approximating the compliancy or resiliency of the vessel. However, reducing the amount of core material in stent 10 can also reduce the radiopacity of the stent.

To increase the radiopacity of stent 10, the stent includes radiopaque portion 16 disposed over core portion 14. Portion 16 includes radiopaque layer 18, which is formed with a radiopaque material. The radiopaque material can be any material with a density and/or linear absorption coefficient sufficient to enhance the radiopacity of stent 10. In embodiments, the radiopaque material has a density and/or linear absorption coefficient to attenuate an incident X-ray beam. In some cases, the radiopaque material has a density of equal to or greater than about 10 g/cc. Examples of radiopaque materials include gold, platinum, palladium, tantalum, iridium, cobalt, titanium, tungsten, stainless steel, Nitinol, and metal alloys containing a sufficient percentage of heavy elements. Radiopaque layer 18 can be, for example, up to about 8 microns thick, e.g., about 6–8 microns, thick. Methods of forming radiopaque layer 18 include, for example, electrodeposition, physical vapor deposition (e.g., sputtering), chemical vapor deposition, galvanizing, and/or dipping (e.g., in molten material).

In some cases, however, the radiopaque materials do not have a desired level of biocompatibility and/or the biocompatibility of the material is unknown (e.g., in the long term). It is believed, for example, that gold may affect (e.g., catalyze) electron transfer in certain undesirable reactions in the body. Accordingly, radiopaque portion 16 includes a relatively inert layer 20 disposed over radiopaque layer 18.

Layer 20 enhances the biocompatibility of stent 10 by providing the stent with a layer (as shown, an outer layer) that can be passivated, e.g., more easily than radiopaque layer 18. For example, layer 20 is capable of reacting (e.g., oxidizing) and forming products, such as oxides, nitrides, and/or carbides, that are more inert, and therefore, more biocompatible, than the material(s) in radiopaque layer 18. Relative to radiopaque layer 18, layer 20 has a lower oxidation potential, i.e., can be more easily oxidized to form a biocompatible product.

In some embodiments, layer 20 includes a mixture (here, an alloy) of the radiopaque material(s) in radiopaque layer 18 and one or more alloying material. The alloying material can be any material capable of forming a mixture with the radiopaque material(s), and forming a product that is more easily passivated than the radiopaque material(s). The alloying material can be, for example, tantalum, titanium, niobium, zirconium, chromium, silicon, rhodium, iridium, platinum, and/or palladium. Any of the alloying materials can be used with any of the radiopaque materials described above.

As an example, for a gold radiopaque layer 18, the alloying material can be titanium. In this example, layer 20 includes an alloy of gold-titanium, such as $Au_{0.30}Ti_{0.70}$, which can be more easily passivated than gold. That is, relative to gold, the gold-titanium alloy can more easily form or be converted to a product, e.g., an oxide, that is relatively inert and biocompatible. In embodiments, for the alloy of gold-titanium ($Au_xTi_y$) x can range from about 0–30%, and y can range from about 70–100%. For example, x can be equal to or greater than about 0%, 5%, 10%, 15%, 20%, or 25%, and/or equal to or less than about 30%, 25%, 20%, 15%, 10%, or 5%. In embodiments, the concentration of titanium, y, can be equal to or greater than about 70%, 75%, 80%, 85%, 90%, or 95%, and/or less than or equal to 100%, 95%, 90%, 85%, 80%, or 75%. Layer 20 can be up to about 10 microns thick, e.g., about 0.1–10 microns thick. Ternary (e.g., Au—Ti—Cr) or higher mixtures or alloy systems can be formed.

In some embodiments, layer 20 can be formed on a pre-formed radiopaque layer 18.

For example, after radiopaque layer 18 is formed, modified layer 20 can be applied on the radiopaque layer by physical vapor deposition, including sputtering and ion beam assisted deposition, chemical vapor deposition, or electrodeposition. Layer 20 can also be formed by forming layers, e.g., alternating layers, of the radiopaque material and the alloying material on layer 18 in a predetermined ratio, and heating the layers (e.g., at elevated, annealing temperatures) to form the alloy by diffuision.

Alternatively or in addition, layer 20 can be formed from a portion of a formed radiopaque layer 18. That is, a portion of the radiopaque layer 18 can be converted to layer 20. For example, a gold-titanium layer 20 can be formed by implanting titanium ions into a formed gold radiopaque layer 18, and annealing the radiopaque layer. As a result, a certain thickness of the radiopaque layer (e.g., in the sub-micron range) is converted to an alloyed modified layer that can be passivated. In another example, a layer of alloy material, e.g., Ti, can be deposited on radiopaque layer 18, e.g., Au, and the layers can be heated, e.g., annealed, to form an alloy, e.g., Au—Ti.

It should be noted that while FIG. 2 shows radiopaque layer 18 and layer 20 as two discrete, well-defined layers, in some embodiments, the interface between the layers is not well defined. As a result, the endoprosthesis can be formed with good adhesion and high durability (e.g., reduced risk of flaking). Corrosion from contact of dissimilar material can also be reduced. The interface may not be well defined, for example, when modified layer 20 is formed from a formed radiopaque layer 18.

In some embodiments, radiopaque portion 16 does not include an interface between two layers. Referring to FIG. 3, a strut 22 of a stent is formed of a relatively radiolucent core 24 surrounded by a relatively radiopaque layer 26. Core 24 is generally the same as core 14 described above. Radiopaque layer 26 includes one or more radiopaque material and one or more alloying material, as described above. In addition, radiopaque layer 26 is formed having a compositional gradient in which the concentration(s) of the alloying material(s) and/or the radiopaque material(s) varies along the thickness of layer 26 (arrows A and B). As an example, for a radiopaque layer 26 formed of a gold-titanium alloy, layer 26 can be relatively gold-rich (or titanium-poor) at surface 28 adjacent to core 24, and relatively gold-poor (or titanium-rich) at outer surface 30. At surface 28, the concentration of the radiopaque material can be about 100%; and at outer surface 30, the concentration of the alloying material can be about 100%. The concentration(s) of the radiopaque material(s)l and/or the alloying material(s) can vary linearly or non-linearly (e.g., exponentially) between surfaces 28 and 30. The concentration(s), e.g., of the alloying material, can increase or decrease from surface 28 to surface 30. In certain embodiments, layer 26 having the compositional gradient can be formed on a radiopaque layer, such as radiopaque layer 18.

Methods of forming compositionally-graded layer 26 include using physical vapor deposition while controlling the source of materials used for deposition. In another method, layer 26 can be formed by forming alternating layers of a radiopaque material and an alloying material in a predetermined ratio, and annealing the layers. For example, referring to FIG. 4, to form a concentration gradient of titanium along layer 26, layers of titanium 27a, 27b, and 27c can be formed alternating with layers of gold 29a, 29b, and 29c. Titanium layer 27a is thicker than layer 27b, which is thicker than layer 27c. Gold layers 29a–29c are of equal thickness. When the layers are subsequently annealed, they can diffuse together and form a gold-titanium alloy in which the concentration of titanium varies along the thickness of layer 26 (here, increasing with increasing distance from core 24).

After layer 20 or 26 is formed, stent 10 can be passivated by exposing the stent to an appropriate environment. For example, stent 10 can be oxidized by heating the stent in an oxidizing atmosphere, such as one containing oxygen and/or water, to form an oxide layer on layer 20 or 26. Nitrides can be formed by heating stent 10 in an atmosphere containing nitrogen, nitrogen-hydrogen, and/or ammonia. Carburizing, e.g., increasing the surface concentration of carbon, can be performed by exposing stent 10, at an elevated temperature, to an atmosphere rich in a hydrocarbon gas, such as methane. Alternatively or in addition, passivation can be performed by electropolishing to produce an oxide-rich surface layer. In some cases, passivation can occur relatively spontaneously, e.g., upon exposure to air, when the oxidation potential is relatively low.

Stent 10 can then be finished, e.g., electropolished to a smooth finish, according to conventional methods. Stent 10 can be finished before passivation. Alternatively, stent 10 can be formed textured.

Stent 10 can then be used, e.g., delivered and expanded, according to conventional methods.

Generally, stent 10 can be self-expandable, balloon-expandable, or a combination of both. Examples of stent 10 and support 12 are described in U.S. Pat. Nos. 5,725,570 (Heath) and 5,234,457 (Andersen), all hereby incorporated by reference.

In other embodiments, stent 10 is a part of a stent-graft. The stent-graft can be a stent attached to a biocompatible, non-porous or semi-porous polymer matrix made of polytetrafluoroethylene (PTFE), expanded PTFE, polyethylene, urethane, or polypropylene. Stent 10 can include a releasable therapeutic agent or a pharmaceutically active compound, such as described in U.S. Pat. No. 5,674,242, and commonly-assigned U.S. Ser. No. 09/895,415, filed Jul. 2, 2001, all hereby incorporated by reference. The therapeutic agents or pharmaceutically active compounds can include, for example, anti-thrombogenic agents, antioxidants, anti-inflammatory agents, anesthetic agents, anti-coagulants, and antibiotics.

The following examples are illustrative and not intended to be limiting.

EXAMPLE

The following example describes ion beam assisted deposition (IBAD) as a method for depositing thin films on a substrate, e.g., a stent.

Figure 5:
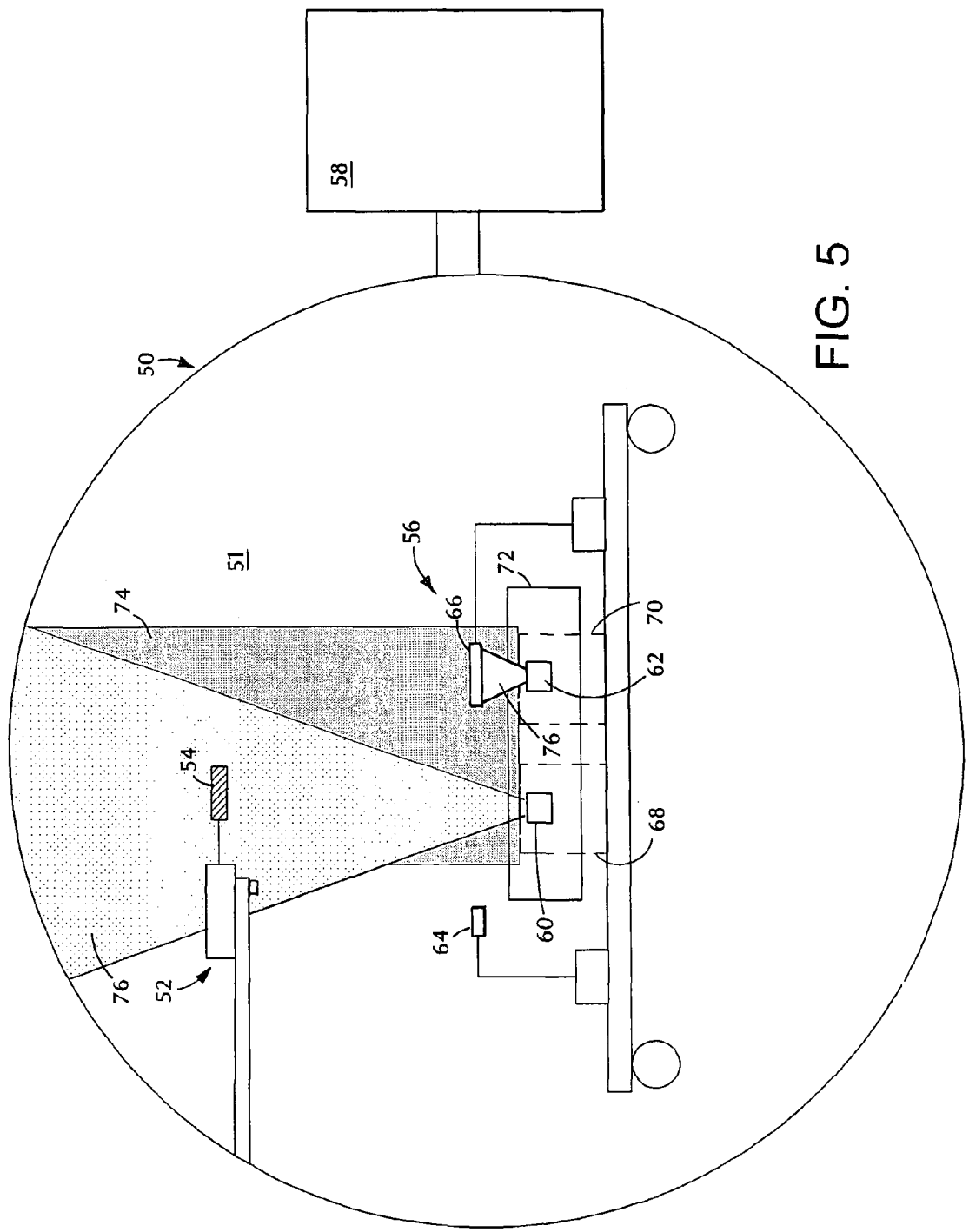
FIG. 5 is a schematic diagram of an embodiment of an ion beam assisted deposition system.

Referring to FIG. 5, an IBAD system 50 generally includes a fixture assembly 52 configured to support a stent 54, and a deposition assembly 56. System 50 is used in a vacuum chamber 51 at pressures of about $1 \times 10^{-4}$–$3 \times 10^{-4}$ Torr, provided in part by a diffusion pump 58.

Deposition assembly 56 includes two crucibles 60 and 62, their respective shutters 64 and 66, two electron beam evaporators 68 and 70, and an ion beam gun 72. Crucibles 60 and 62, e.g., made of graphite, contain materials to be deposited, such as gold and titanium. Electron beam evaporators 68 and 70 are configured to generate a flow of electrons that can be focused (e.g., using magnetic fields) on the materials in crucibles 60 and 62, respectively, to melt and to evaporate the materials to form thermally evaporated materials 76.

Evaporators 68 and 70 can have water-cooled jackets that cool crucibles 60 and 62, respectively. Ion beam gun 72 is configured to receive a flow of argon (e.g., 2–4 sccm) and to ionize the argon to form a plasma 74. Plasma 74 is accelerated out of ion beam gun 72 to stent 54 using magnets (not shown). Shutters 64 and 66 can be moved, e.g., swiveled, to allow or to block the flow of evaporated material 76 from crucibles 60 and 62, respectively.

Fixture assembly 52 is generally configured to allow stent 54 to be uniformly coated with evaporated material 76. Typically, the thermal evaporation process can deposit a film of material 76 on a substrate that is in a line of sight of crucible 60 or 62. To provide uniform coverage on stent 54, the stent is rotated during deposition. In embodiments, stent 54 is placed on a rotatable spindle. The friction between the stent and the spindle can hold the stent in place during rotation to provide a coated stent without contact points. Alternatively, stent 54 can be clipped to a rotatable shaft.

A quartz crystal 78 is used to determine the thickness of the deposited material. Crystal 78 is interfaced to a controller (not shown) and oscillated. The controller is calibrated such that the thickness of material deposited on crystal 78 (and thus also stent 54) can be calculated by measuring the change in the oscillation frequency of the crystal.

A method of coating using IBAD will now be described.

Stent 54, e.g., a Nitinol or stainless steel stent, is thoroughly chemically cleaned. For example, stent 54 can be cleaned in a solvent (such as isopropyl alcohol or acetone) and a degreaser, and rinsed with deionized water. Heat and/or agitation, e.g., using ultrasonic energy, can be used to clean stent 54. Stent 54 is then placed on fixture assembly 52, which is then placed in vacuum chamber 51, with the stent about two feet from crucibles 60 and 62.

Stent 54 is then subjected to a sputter cleaning. Chamber 51 is evacuated to a pressure of about $1 \times 10^{-5}$ Torr, and ion beam gun 72 is activated. Ion beam gun 72 ionizes argon gas to form plasma 74, and the plasma is accelerated to stent 54 to sputter clean/etch the surface of the stent. The angle of incidence for plasma 74 can be about 45–90°, e.g., about 70°. In embodiments, stent 54 is sputter cleaned for about 20–30 minutes. An estimated 100–300 angstroms of material can be removed.

A first material, e.g., gold in crucible 60, is then deposited. During the final ten minutes of sputter cleaning, electron beam evaporators 68 and 70 are slowly ramped up.

Shutters 64 and 66 are over their respective crucibles 60 and 62, so no material can deposit on stent 54. After sputter cleaning is complete and the material to be deposited is molten, shutter 64 moves, e.g., swivels, to allow evaporated material to coat stent 54. The surface of stent 54 is simultaneously bombarded with plasma 74. It is believed that as ions of the first material deposit on stent 54, plasma 74 transfers energy to the ions, freeing some ions from the surface of the stent and allowing some ions to migrate on the stent surface. As a result, it is believed that a composite including the first material is formed with enhanced density.

Figure 6:
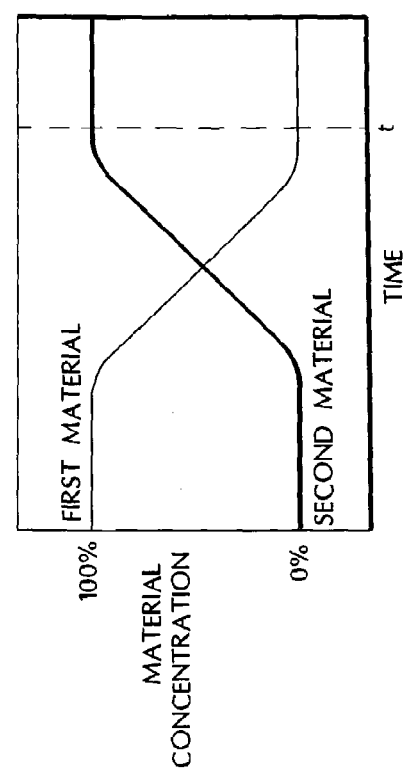
FIG. 6 is a plot of material concentration as a function of time.

A second material, e.g., titanium, tantalum, or platinum, is then deposited. After the thickness of the first material coated on stent 54 reaches, e.g., about 200–500 angstroms, shutter 66 is moved to allow the second material (in crucible 62) to co-deposit with the first material. The concentrations of each material can be controlled by adjusting the power to evaporators 68 and 70. For example, referring to FIG. 6, initially the concentration of the first material is relatively high, and the second material is then slowly introduced. In embodiments, at time t, shutter 64 is moved to prevent the first material from depositing on stent 54, and a pure layer of the second material is deposited over the alloy layer (i.e., the layer having the first and second materials). Then, stent 54 is allowed to cool, chamber 51 is returned to atmospheric pressure, and the stent is removed from the chamber.

In embodiments, stent 54 is then annealed. Annealing can promote diffusion between the layers of materials and/or the layers and the stent substrate, and can strengthen bonding or adhesion between the layers. In some cases, a Nitinol stent can be annealed at about 300–400° C., and a stainless steel stent can be annealed at about 500–1000° C. Annealing times can vary, e.g., from a few minutes to days, depending, for example, on the diffusion of the materials in stent 54, which can be temperature-dependent.

FIG. 7 shows ranges for some process parameters.

A stent was coated with titanium using the procedures described above. The process parameters are shown in FIG. 8.

A stent was coated with a platinum-gold using the procedures described above. The process parameters are shown in FIG. 9. The platinum-gold gradient was similar to that shown in FIG. 6.

OTHER EMBODIMENTS

In other embodiments, one or more intermediate layers can be formed between core 14 or 24 and radiopaque layer 18 or 26, i.e., at least a portion of the core and the radiopaque layer do not contact. For example, in embodiments in which there is lattice mismatch between the core and the radiopaque layer, intermediate layer(s) can be selected to have intermediate lattice parameters to serve as buffer layer(s), thereby reducing (e.g., minimizing) stress between the core and the radiopaque layer. The intermediate layer(s) can be, for example, a mixture of the core material and the radiopaque material.

Layer 20 may not include the radiopaque material(s) in radiopaque layer 18. For example, a radiopaque layer may include gold, while layer 20 includes a material that can be passivated, such as a platinum-titanium alloy.

Radiopaque layer 18, layer 20, and/or layer 26 can cover all or only one or more selected portions of a stent. For example, radiopaque layer 18, layer 20, and/or layer 26 may be formed only on one or more end portions of the stent.

In some embodiments, other types of layers can be formed on layer 20 or 26. For example, one or more selected portions of a stent may include a magnetopaque (i.e., visible by magnetic resonance imaging (MRI)) material on layer 20 or 26. Suitable magnetopaque materials include, for example, non-ferrous metal-alloys containing paramagnetic elements (e.g., dysprosium or gadolinium) such as terbium-dysprosium, dysprosium, and gadolinium; non-ferrous metallic bands coated with an oxide or a carbide layer of dysprosium or gadolinium (e.g., $Dy_2O_3$ or $Gd_2O_3$); non-ferrous metals (e.g., copper, silver, platinum, or gold) coated with a layer of superparamagnetic material, such as nanocrystalline $Fe_3O_4$, $CoFe_2O_4$, $MnFe_2O_4$, or $MgFe_2O_4$; and nanocrystalline particles of the transition metal oxides (e.g., oxides of Fe, Co, Ni).

In other embodiments, radiopaque layer 18, layer 20, and/or layer 26 may be formed on medical devices other than stents and stent-grafts, for example, those where radiopacity is desired such as orthopedic implants.

All publications, applications, and patents referred to herein are incorporated by reference in their entirety.

Other embodiments are within the claims.

What is claimed is:

1. A stent, comprising:
   a member including
      a first portion; and
      a second portion disposed outwardly of the first portion and having
         a first layer including a radiopaque material that is more radiopaque than the first portion, wherein the radiopaque material is selected from the group consisting of gold, platinum, and palladium,
         a second layer comprising an alloy comprising the radiopaque material and a second material, and
         a third layer comprising an oxidized form of the alloy.

2. The stent of claim 1, wherein the radiopaque material is platinum.

3. The stent of claim 1, wherein the second material is selected from the group consisting of titanium, chromium, palladium, niobium, and silicon.

4. The stent of claim 1, wherein the first portion comprises a material selected from the group consisting of stainless steel and nickel-titanium alloy.

5. The stent of claim 1, wherein the first portion is the innermost portion of the member.

6. The stent of claim 1, wherein the first portion contacts the second portion.

7. The stent of claim 1, further comprising a third portion between the first portion and the second portion.

8. The stent of claim 1, further comprising a polymeric layer on the member.

9. The stent of claim 1, further comprising a drug-releasing layer on the member.

10. A stent, comprising:
    a member including
       a first portion having
          a first layer including a radiopaque material, wherein the radiopaque material is selected from the group consisting of gold, platinum, and palladium, and
          a second layer comprising an alloy comprising the radiopaque material and a second material, and
          a third layer comprising an oxidized form of the alloy.

11. The stent of claim 10, wherein the radiopaque material is platinum.

12. The stern of claim 10, wherein the second material is selected from the group consisting of titanium, chromium, palladium, niobium, and silicon.

13. The stent of claim 10, wherein the third layer is the outermost layer.

14. The stent of claim 10, further comprising a polymeric layer on the member.

15. The stent of claim 10, further comprising a drug-releasing layer on the member.

16. The stent of claim 10, wherein the oxidized form of the alloy comprises an oxide, a nitride, or a carbide.

17. The stent of claim 10, wherein the oxidized form of the alloy comprises an oxide.

18. The stent of claim 1, wherein the oxidized form of the alloy comprises an oxide, a nitride, or a carbide.

19. The stent of claim 1, wherein the oxidized form of the alloy comprises an oxide.

20. A stent, comprising:a member including
    an innermost first portion; and
    a second portion disposed outwardly of the first portion and having
       a first layer including a radiopaque material that is more radiopaque than the first portion,
       a second layer comprising an alloy comprising the radiopaque material and a second material, wherein at least one of the radiopaque material and the second material comprises iridium, and
    a third layer comprising an oxidized form of the alloy, the oxidized form comprising an oxide.

* * * * *

UNITED STATES PATENT AND TRADEMARK OFFICE
CERTIFICATE OF CORRECTION

PATENT NO. : 7,297,157 B2 Page 1 of 1
APPLICATION NO. : 10/629934
DATED : November 20, 2007
INVENTOR(S) : Verivada Chandrasekaran, Karl Morris Schmidt and Christopher Torres Molina It is certified that error appears in the above-identified patent and that said Letters Patent is hereby corrected as shown below:

Title Page, References Cited, U.S. Patent Documents, please insert

--6,554,855   4/2003   Dong--;

Column 10, line 21, please delete "stern" and insert --stent-- therefor.

Signed and Sealed this

Ninth Day of March, 2010

David J. Kappos
*Director of the United States Patent and Trademark Office*